United States Patent [19]

Tieman

[11] 4,360,689

[45] Nov. 23, 1982

[54] α-HALOBENZYL ESTERS

[75] Inventor: Charles H. Tieman, Modesto, Calif.

[73] Assignee: Shell Oil Company, Houston, Tex.

[21] Appl. No.: 148,872

[22] Filed: May 12, 1980

[51] Int. Cl.³ .................. C07C 69/612; C07C 121/75; C07D 317/60
[52] U.S. Cl. .................................. 560/55; 260/465 D; 549/447; 560/8; 560/9; 560/20; 560/81; 560/101; 560/105
[58] Field of Search ................. 560/55, 105, 122, 124, 560/221, 255, 8, 9, 20, 81, 101; 260/465 D; 549/447

[56] References Cited

U.S. PATENT DOCUMENTS

| | | | |
|---|---|---|---|
| 4,277,617 | 7/1981 | Martel et al. | 560/124 |
| 4,315,868 | 2/1982 | Martel et al. | 260/465 D |

FOREIGN PATENT DOCUMENTS

| | | |
|---|---|---|
| 1944 | 5/1979 | European Pat. Off. . |
| 6354 | 1/1980 | European Pat. Off. . |

*Primary Examiner*—Dolph H. Torrence

[57] ABSTRACT

New α-halobenzyl esters, intermediates for α-cyanobenzyl pyrethroid esters, are prepared by treating a benzaldehyde derivative with a pyrethroid acid halide. The resulting α-halobenzyl ester is treated with a water-soluble compound capable of generating cyanide ions ($CN^-$) to give the corresponding α-cyanobenzyl esters.

8 Claims, No Drawings

α-HALOBENZYL ESTERS

BACKGROUND OF THE INVENTION

1. Field of the Invention

The present invention is directed to new α-halobenzyl esters useful as intermediates in the preparation of α-cyanobenzyl pyrethroid esters.

2. Description of the Prior Art

U.S. Pat. Nos. 3,835,176, 3,996,244 and 4,024,163 describe α-cyanobenzyl esters of cyclopropanecarboxylic acids and phenylacetic acids, which are useful as insecticides having quick knockdown activity, low persistence of toxic residues and low mammalian toxicity. Because of the interest in these compounds for pest control, considerable efforts have been made to find new synthesis routes to them. The present application is accordingly directed to a new method of preparing α-cyanobenzyl esters and new intermediates to be used in that method.

SUMMARY OF THE INVENTION

Compounds of the formula I:

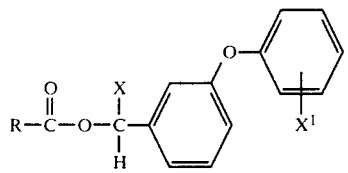

I wherein

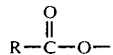

is the residue of a pyrethroid acid and X is a chlorine, flourine or bromine atom; and $X^1$ is a hydrogen, chlorine, fluorine or bromine atom, are new compounds, useful as intermediates to the corresponding α-cyanobenzyl pyrethroid ester pesticides.

Examples of α-halobenzyl esters of formula I are (a) α-chloro-3-phenoxybenzyl 2-(2,2-dichlorovinyl)-3,3-dimethylcyclopropanecarboxylate;
(b) α-bromo-3-phenoxybenzyl 2-(2,2-dibromovinyl)-3,3-dimethylcyclopropanecarboxylate;
(c) α-chloro-3-phenoxybenzyl 2,2,3,3-tetramethylcyclopropanecarboxylate;
(d) α-bromo-3-phenoxybenzyl isopropyl-(4-chlorophenyl)acetate;
(e) α-chloro-3-phenoxybenzyl isopropyl-(4-difluoromethoxyphenyl)acetate;
(f) α-bromo-3-phenoxybenzyl 3,3-dimethyl-spiro-(1-indene) cyclopropane-2-carboxylate;
(g) α-chloro-3-phenoxybenzyl (2-chloro-4-trifluoromethyl)phenylamino)-2-isopropylacetate;
(h) α-bromo-3-(4-chlorophenoxy)benzyl 2-(2,2-dichlorovinyl)-3,3-dimethylcyclopropanecarboxylate;
(i) α-chloro-3-(4-fluorophenoxy)benzyl 2-(2,2-dichlorovinyl)-3,3-dimethylcyclopropanecarboxylate;
(j) α-bromo-3-phenoxybenzyl 2-(1,2-dibromo-2,2-dichloroethyl)-3,3-dimethylcyclopropanecarboxylate;
(k) α-fluoro-3-phenoxybenzyl 2-(2-(trifluoromethyl)-2-chlorovinyl)-3,3-dimethylcyclopropanecarboxylate.

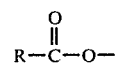

is the residue of a pyrethroid acid, suitably one in which R is an optionally substituted acyclic or monocyclic group containing from 3 to 35 carbon atoms. Suitably, R is selected from the group of formulas II–VIII:

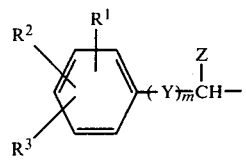

II

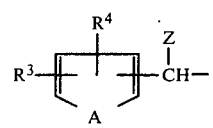

III

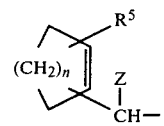

IV

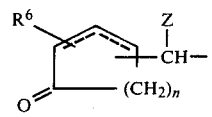

V

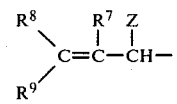

VI

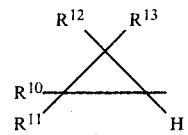

VII

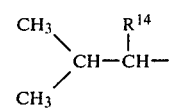

VIII wherein $R^1$ and $R^2$ are individually hydrogen, halogen, cyano, nitro, lower alkyl, lower alkenyl, lower alkynyl, lower alkoxy, lower alkoxyalkyl, halo-substituted lower alkyl, halo-substituted lower alkenyl, halo-substituted lower alkynyl, halo-substituted lower alkoxy, lower alkylthio, lower alkylsulfinyl, lower alkylsulfonyl, halo-substituted lower alkylthio, halo-substituted lower alkylsulfinyl, halo-substituted lower alkylsulfonyl, acyl, acyloxy, lower alkoxycarbonyl, lower alkenyloxycarbonyl, lower alkynyloxycarbonyl; or $R^1$ and $R^2$ together are a methylenedioxy, tetramethylene or trimethylene group; $R^3$ and $R^4$ are individually hydrogen, halogen, cyano, nitro, lower alkyl, lower alkenyl, lower alkynyl, lower alkoxy, lower alkoxyalkyl, halogen-substituted lower alkyl, halogen-substituted lower alkenyl, halogen-substituted lower alkynyl, lower alkylthio, lower alkylsulfonyl, acyl, acyloxy, lower alkoxycarbonyl, lower alkenyloxycarbonyl or lower alkynyloxycarbonyl group; $R^5$ represents hydrogen, halogen, cyano, nitro or lower alkyl group; m is 0 or 1; $R^6$ represents hydrogen, halogen, cyano, nitro or lower alkyl group; n is an integer of from 1 to 3; and the dotted line in the formula (V) represents a double bond present at a position conjugated or non-conjugated with the ketone (C=O); $R^7$, $R^8$ and $R^9$ constitute a plane together with the double bond at β-γ position of the ester group, and are individually hydrogen, lower alkyl, lower alkenyl, lower alkynyl, halogen, acyl or acyloxy; $R^{10}$ and $R^{11}$ are individually lower alkyl or halogen; $R^{12}$ and $R^{13}$ are lower alkyl or when $R^{12}$ is hydrogen then $R^{13}$ is lower alkenyl, halo-substituted lower alkenyl or —CH=N—$OR^{15}$ in which $R^{15}$ is lower alkyl or (cycloalkyl)alkyl, $R^{14}$ is lower alkenyl, halo-or lower alkyl-substituted aralkyl or lower alkyl; A is oxygen or sulfur and Y is —NH—; Z represents a straight or branched lower alkyl, lower alkenyl, lower alkynyl, lower alkoxy, halogen-substituted lower alkyl, halogen-substituted lower alkenyl group or an alicyclic group having 3 to 7 carbon atoms.

When R is a group of the formula IX:

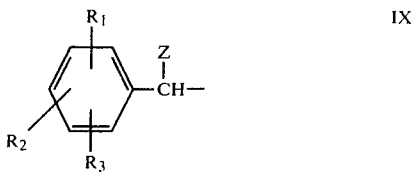

preferably, $R_1$ is a member selected from the group consisting of hydrogen, methoxy, ethoxy, acetoxy, methylsulfinyl, difluoromethoxy, trifluoromethoxy, $C_1$–$C_4$ alkyl, trifluoromethyl, allyl, acetyl, ethoxycarbonyl, methylthio, chlorine, fluorine, iodine, isopropenyl, propargyl, methoxymethyl, ethoxymethyl, chloroallyl, butyryl, butylthio, allyloxycarbonyl, nitro and methoxycarbonyl; $R_2$ is a member selected from the group consisting of hydrogen, methyl, methoxy, chlorine and bromine; or $R^1$ and $R^2$ together are methylenedioxy, trimethylene or tetramethylene, $R_3$ is hydrogen or methyl; Z is a member selected from the group consisting of $C_1$–$C_4$ alkyl, ethoxy, allyl, bromoethyl, cyclohexyl, cyclopropylmethyl, isopropenyl, propargyl, trifluoromethyl and cyano.

Because of the utility of the ultimate pyrethroid esters, $R^1$ is preferably methoxy, ethoxy, chlorine, fluorine, methyl, ethyl, isopropyl, tert-butyl, difluoromethoxy or trifluoromethoxy, $R^2$ and $R^3$ are hydrogen, and Z is isopropyl.

When R is a group of formula VII, preferably $R^{10}$ and $R^{11}$ are each methyl and when $R^{12}$ is hydrogen then $R^{13}$ is isobutenyl, monochlorovinyl, dichlorovinyl, dibromovinyl, (cyclobutylmethoxyimino)methyl, sec-butoxyiminomethyl or neopentoxyiminomethyl.

X in formula I is preferably chlorine or bromine.

The α-halobenzyl esters of the invention are prepared by known esterification reactions, for example, by a process which comprises reacting an acid halide of the formula:

wherein R and X have the meanings defined above with a 3-phenoxybenzaldehyde, preferably in the presence of an acidic catalyst.

An acid or acidic-acting material which will not interfere with the reaction can be used as a catalyst. Suitable inorganic acids include the hydrohalogenic acids, such as hydrochloric and hydrobromic acids; the sulfur acids, such as sulfuric and fluorosulfonic acids; the phosphorus acids, such as phosphoric acid. Suitable organic acids include the lower alkanesulfonic acids, such as methanesulfonic acid.

Preferably, the catalyst is a Lewis acid: that is, a compound which will accept one or more pairs of electrons from another compound to form a coordinate covalent bond. Suitably, the Lewis acid is derived from an element of Group IIIA of the Periodic Table of Elements (Lange, "Handbook of Chemistry", 8th Edition, pages 56–57) titanium, tin, antimony, tantalum, rhenium, iron or zinc. These include inorganic compounds, derived from boron, aluminum, gallium, indium, thallium, zinc, titanium, antimony, iron and the like. Generally, the inorganic Lewis acid halides and cyanides are preferred. These include boron trichloride, boron tribromide, aluminum chloride, aluminum bromide, gallium trichloride, gallium tribromide, titanium tetrachloride, titanium tetrabromide, stannic chloride, stannic bromide, antimony pentachloride, tantalum pentachloride, rhenium pentachloride, ferric chloride and especially zinc salts, such as zinc chloride, zinc iodide or zinc cyanide.

Optimum amounts of Lewis acid depend on the particular catalyst chosen, the solvent and the reaction components as well as the reaction time and product purity desired. Usually, the molar ratio of catalyst to 3-phenoxybenzaldehyde is from 1:5 to 1:500, preferably 1:10 to 1:100.

A solvent is generally not required for the reaction to proceed. However, any solvent inert to the reaction may be used.

The molar ratio of the acid halide to 3-phenoxybenzaldehyde can be varied, e.g., from 1:3 to 3:1, but is preferably about 1:1.

The preferred reaction temperature is such as to constitute room temperatures or below if at normal atmospheric pressure and will naturally vary as to the nature of the composition of the reaction mixture.

The various ingredients of the reaction mixture are contacted, preferably with agitation, e.g., stirring. The acid halide may also be gradually added to a mixture of the other starting compound and reaction ingredients.

Conventionally, after a (Lewis) acid catalyzed reaction has been completed, or has been carried out to a desired degree of conversion, it can be advantageous to inactivate the (Lewis) acid before any components of the reaction mixture are isolated. This inactivation of the (Lewis) acid can be conveniently accomplished by extraction of the reaction mixture with water.

The products of the process of the invention are then recovered by suitable techniques of filtration, distillation and the like.

The 3-phenoxybenzaldehyde reactant is well known in the art as are the acid halides, for example, in U.S. Pat. Nos. 3,835,176, 3,996,244, 4,024,163, 4,042,710, 4,110,360 and German Pat. No. 2,753,605. The α-cyanobenzyl esters, which are made from the novel α-halobenzyl esters are also known in the art as exemplified by the disclosures of the above-mentioned patents.

The present invention also includes a process for the preparation of α-cyanobenzyl esters of the formula X:

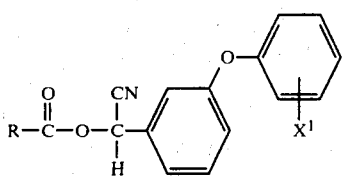

wherein

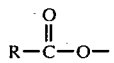

is the residue of a pyrethroid acid, which comprises treating an α-halobenzyl ester of the formula:

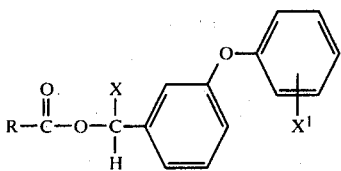

wherein

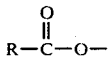

has the meaning earlier defined in regard to formula I and X is a chlorine, fluorine or bromine atom with a compound capable of generating cyanide ions in the presence of an inert solvent and optionally water.

Examples of α-cyanobenzyl esters prepared by the above process include:

(a) α-cyano-3-phenoxybenzyl 2-(2,2-dichlorovinyl)-3,3-dimethylcyclopropanecarboxylate;

(b) α-cyano-3-phenoxybenzyl 2-(2,2-dibromovinyl)-3,3-dimethylcyclopropanecarboxylate;

(c) α-cyano-3-phenoxybenzyl 2,2,3,3-tetramethylcyclopropanecarboxylate;

(d) α-cyano-3-phenoxybenzyl isopropy-(4-chlorophenyl)acetate;

(e) α-cyano-3-phenoxybenzyl isopropyl-(4-(difluoromethoxy)phenyl)acetate;

(f) α-cyano-3-phenoxybenzyl 3,3-dimethyl-spiro-(1-indene) cyclopropane-2-carboxylate;

(g) α-cyano-3-phenoxybenzyl (2-chloro-4-(trifluoromethyl)phenylamino)-2-isopropylacetate;

(h) α-cyano-3-(4-chlorophenoxy)benzyl 2-(2,2-dichlorovinyl)-3,3-dimethylcyclopropanecarboxylate;

(i) α-cyano-3-(4-fluorophenoxy)benzyl 2-(2,2-dichlorovinyl)-3,3-dimethylcyclopropanecarboxylate;

(j) α-cyano-3-phenoxybenzyl 2-(1,2-dibromo-2,2-dichloroethyl)-3,3-dimethylcyclopropanecarboxylate;

(k) α-cyano-3-phenoxybenzyl 2-(2-(trifluoromethyl)-2-chlorovinyl)-3,3-dimethylcyclopropanecarboxylate.

The solvent is any organic solvent inert to the reaction and mixtures of such solvents with each other or with water. Suitable solvents are hydrocarbons and chlorinated hydrocarbons, for example, aromatic hydrocarbons and chlorinated hydrocarbons, for example, benzene, toluene, o-, m- and p-xylene, the trimethylbenzenes, dichloromethane, 1,2-dichloroethane, chloroform, mono-chlorobenzene and 1,2-dichlorobenzene. Acetonitrile is also a very good solvent. Very good results have been obtained with toluene.

The esters of formula X may be prepared in the presence or absence of a catalyst. The catalyst may be any reagent which is capable of accelerating the reaction in a homogeneous system or a two-phase system.

Preferably, the catalyst is a quaternary onium phase-transfer compound of formula XI:

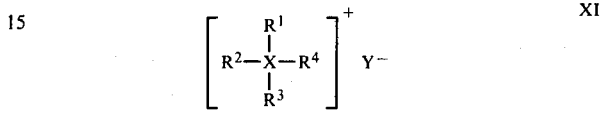

wherein X represents a nitrogen, phosphorus or arsenic atom and each of the groups $R^1$, $R^2$, $R^3$ and $R^4$ represents a monovalent ion.

Preferably, $R^1$, $R^2$, $R^3$ and $R^4$ each independently is an alkyl group of 1 to 18 carbon atoms, an aralkyl or alkaryl group of 7 to 10 carbon atoms or an aryl group of 6 to 12 carbon atoms.

In the above formula, Y can be hydroxide, halide, alkyl sulfate, alkylsulfonate, tetrafluoroborate, phosphate, nitrate or alkyl- or aryl-carboxylate. For example, Y can be chloride, bromide, iodide, methyl sulfate, ethyl sulfate, tosylate, acetate, formate, citrate, tartrate, benzoate or the like.

Examples of suitable onium compounds are tetra-n-butylammonium bromide, tetra-n-butylammonium chloride, methyltri-2-methylphenylammonium chloride, tetramethylphosphonium iodide, tetra-n-butylphosphonium bromide, methyltriphenylarsonium iodide, and methyltrioctylammonium chloride. Further suitable onium compounds are described in U.S. Pat. Nos. 3,917,667, 4,008,287 and 4,012,430. Very good results have been obtained with quaternary ammonium compounds.

The onium compound may be a hydroxide or salt and used as the functional portion of a strongly basic anion exchange resin having a structural portion (polymer matrix) and a functional portion (ion-active group). Of special importance are polystyrene resins, such as copolymers of aromatic monovinyl compounds and aromatic polyvinyl compounds, particularly styrene/divinylbenzene copolymers. The functional portion is a quaternary ammonium, phosphonium or arsonium group. Examples of strongly basic anion exchange resins which may be employed are those derived from trimethylamine (such as the products known under the trade names of "Amberlite IRA-400", "Amberlite IRA-401", "Amberlite IRA-402", "Amberlite IRA-900", "Duolite A-101-D", "Duolite ES-111", "Dowex 1", "Dowex 11", "Dowex 21K" and "Ionac A-450" (all ten tradenames are trademarks) and those derived from dimethylethanolamine (such as the products known under the trade names of "Amberlite IRA-410", "Amberlite IRA-911", "Dowex 2", "Duolite A-102-D", "Ionac A-542" and "Ionax A-550" (all six trade names are trademarks).

More particularly, one preferred subclass of catalysts of formula XI are those in which $R^1$, $R^2$, $R^3$ and $R^4$ each independently is an alkyl group of 1 to about 8 carbon atoms such as methyltrioctylammonium chloride, tributylammonium bromide, tetra-n-butylammonium hydroxide, bromide or chloride, methyl-tri-2-methylheptylammonium chloride, tetramethylammonium bromide, tetrabutylphosphonium bromide or tetraethylammonium bromide. Other suitable catalysts of this type are known under the trade names "Hyamine 1663", "Hyamine 2389", "Hyamine 3500", "Aliquat 336" and "Adogen 464" (all five trade names are trademarks).

Another preferred subclass of catalysts of formula XI are those containing one or more phenyl or benzyl groups as $R^1$, $R^2$, $R^3$ and $R^4$ such as benzyltriethylammonium chloride or ethyltriphenylphosphonium bromide or the like.

Other suitable phase transfer catalysts are macrocyclic polyethers known as "crown ethers". These compounds, together with their preparation, are described in the literature, for example, in Tetrahedron Letters No. 18 (1972), pp 1793–1796, and are commonly designated by reference to the total number of atoms forming the macrocyclic ring together with the number of oxygen atoms in that ring. Thus, the macrocyclic polyether whose formal chemical name is 1,4,7,10,13,16-hexaoxacyclooctadecane is designated as "18-crown-6". Other examples of suitable macrocyclic polyethers are 3,4-benzo-1,6,9,12,15,18,21-heptaoxacyclotricos-3-ene and 3,4-benzo-1,6,9,12-tetraoxacyclotetradec-3-ene. 18-Crown-6 is particularly suitable. Further suitable macrocyclic polyethers and their preparation are described in U.S. Pat. No. 3,562,295, British Pat. No. 1,108,921 and Netherlands publication 7602,604.
1,4,7,10,13,16-hexaoxacyclooctadecane,
1,4,7,10,13-pentaoxacyclopentadecane,
1,4,7,10,13,16,19-heptaoxacycloheneicosane,
1,4,7,10,13,16,19,22-octacyclotetracosane, and
1,4,7,10,13,16,19,22,25,27-decaoxacyclotricontane.

In synthesis of the α-cyanobenzyl ester of formula X, the molar ratio of the catalyst to the α-halobenzyl ester of formula I may vary within wide limits, but is suitably from about 1:5 to about 1:10,000. Low molar ratios will require long reaction times, while high molar ratios will increase the cost involved in producing a given quantity of ester. Thus, the choices of reaction time and molar ratio of catalyst to α-halobenzyl ester are interdependent and will, in any individual instance, be dictated by global economic factors. Very good results are usually obtained at molar ratios of from about 1:10 to 1:500 or even from about 1:10 to about 1:100.

The molar ratio of compound capable of generating cyanide ions to α-halobenzyl ester is suitably from 1.5:1 to 1.0:1.0 and preferably from 1.3:1 to 1.02:1.00. By "compound capable of generating cyanide ions" is meant a water-soluble salt of hydrogen cyanide. Of these water-soluble cyanides, alkali metal cyanides and alkaline-earth-metal cyanides are preferred. Sodium cyanide is preferred.

The reaction is conducted by agitating, e.g. stirring, a mixture of the total amounts of the starting materials. The temperature at which the reaction is conducted is suitably above 0° C. at normal pressures, and is preferably in the range of from about 10° to about 50° C. Very good results are obtained at temperatures between about 15° to about 40° C. Normal pressures can be used.

It should be noted that optical isomers, cis-trans isomers and other kinds of geometric isomers of the compounds of formulas I and X are within the scope of the present invention as well as the racemates and mixtures of isomers, such as diasteroisomer and enantiomer pairs.

The various isomers of the compounds of formula X may have different insecticidal, acaricidal and/or knockdown properties. Accordingly, a desired isomer or mixture of isomers of the α-cyanobenzyl ester of formula X may be obtained by using as starting materials the appropriate corresponding isomer or mixture of isomers of the α-halobenzyl ester of formula I.

ILLUSTRATIVE EMBODIMENTS

The invention is illustrated by the following embodiments which describe the preparation of the new α-halobenzyl esters and their conversion into the corresponding α-cyanobenzyl esters. The embodiments are presented for the purpose of illustration only and should not be regarded as limiting the invention in any way. The identity of the products was confirmed by elemental, infrared and nuclear magnetic resonance spectral (NMR) analyses as necessary.

EMBODIMENT I

α-Bromo-3-phenoxybenzyl
α-isopropyl-p-chlorophenylacetate

A mixture of 20.1 ml of α-isopropyl-p-chlorophenylacetyl bromide and 17.2 ml of 3-phenoxybenzaldehyde was stored at 5° C. for two days and then diluted with 70 ml of pentane. After five additional days at 5° C., filtration of the resulting reaction mixture afforded 34.7 g of the desired solid α-bromobenzyl ester product as identified by IR, NMR and elemental analyses.

EMBODIMENT II

α-Chloro-3-phenoxybenzyl
α-isopropyl-p-chlorophenylacetate

A mixture of 10.0 ml of α-isopropyl-p-chlorophenylacetyl chloride, 8.0 ml of 3-phenoxybenzaldehyde and 0.2 g of zinc chloride was stirred for 16 hours at room temperature. The resulting reaction mixture was diluted with pentane, washed with water, dried with magnesium chloride and cooled to −10° C. Filtration of the resulting mixture afforded 6.6 g of the desired α-chlorobenzyl ester product as a solid, m.p. 49°–53° C., consisting mainly of one of the enantiomer pairs according to NMR spectral analysis. Evaporation of the filtrate gave 12.1 g of a yellow syrup consisting mainly of the other enantiomer pair of the α-chlorobenzyl ester. Identification of the products was confirmed by IR spectra and elemental analyses.

EMBODIMENT III

Preparation of α-cyano-3-phenoxybenzyl
α-isopropyl-p-chlorophenylacetate from
α-bromo-3-phenoxybenzyl
α-isopropyl-p-chlorophenylacetate A mixture of 1.1 g of α-bromo-3-phenoxybenzyl α-isopropyl-p-chlorophenylacetate prepared by procedures similar to those of Embodiment I, 0.25 g of sodium cyanide, 0.1 g of 18-crown-6 (macrocyclic polyether) and 10 ml of acetonitrile was stirred for one day at ambient temperature. The resulting reaction mixture was diluted with methylene chloride, washed with water, dried with magnesium sulfate and evaporated to afford 1.0 g of the desired α-cyanobenzyl ester product, as confirmed by NMR spectra.

EMBODIMENT IV

Preparation of α-cyano-3-phenoxybenzyl α-isopropyl-p-chlorophenylacetate from α-bromo-3-phenoxybenzyl α-isopropyl-p-chlorophenylacetate A mixture of 2.3 g of α-bromo-3-phenoxybenzyl α-isopropyl-p-chlorophenylacetate, 1.3 g of tetramethylammonium cyanide and 20 ml of methylene chloride was stirred for 40 minutes, washed with water, dried (MgSO₄) and evaporated to leave an oil having the NMR spectra of the desired α-cyanobenzyl ester product.

EMBODIMENT V

Preparation of α-cyano-3-phenoxybenzyl α-isopropyl-p-chlorophenylacetate from α-bromo-3-phenoxybenzyl α-isopropyl-p-chlorophenylacetate A mixture of 0.5 g of α-bromo-3-phenoxybenzyl α-isopropyl-p-chlorophenylacetate, 3 ml of methylene chloride, 1 ml of water, 0.5 g of sodium cyanide and a catalytic amount of tetrabutylammonium hydrogen sulfate was stirred for 2 hours. The organic phase was separated, dried (MgSO₄) and evaporated to leave an oil with the IR and NMR spectra of the desired α-cyanobenzyl ester product.

I claim:

1. A compound of the formula:

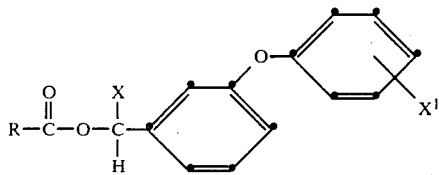

wherein X is a chlorine, flourine, or bromine atom; $X^1$ is a hydrogen atom; and R is a group selected from formula IX:

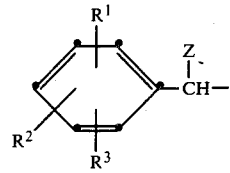

wherein $R_1$ is a member selected from the group consisting of hydrogen, methoxy, ethoxy, acetoxy, methylsulfinyl, difluoromethoxy, trifluoromethoxy, $C_1$–$C_4$ alkyl, trifluoromethyl, allyl, acetyl, ethoxycarbonyl, methylthio, chlorine, fluorine, iodine, isopropenyl, propargyl, methoxymethyl, ethoxymethyl, chloroallyl, butyryl, butylthio, allyloxycarbonyl, nitro and methoxycarbonyl; $R^2$ is a member selected from the group consisting of hydrogen, methyl, methoxy, chlorine and bromine; or $R^1$ and $R^2$ together are methylenedioxy, trimethylene or tetramethylene; $R_3$ is hydrogen or methyl; Z is a member selected from the group consisting of $C_1$–$C_4$ alkyl, ethoxy, allyl, bromoethyl, cyclohexyl, cyclopropylmethyl, isopropenyl, propargyl, trifluoromethyl and cyano.

2. A compound according to claim 1 wherein $R^1$ is methoxy, ethoxy, chlorine, fluorine, methyl, ethyl, isopropyl, tert-butyl, difluoromethoxy or trifluoromethoxy; $R^2$ and $R^3$ are hydrogen and Z is isopropyl and X is chlorine or bromine.

3. A compound of the formula

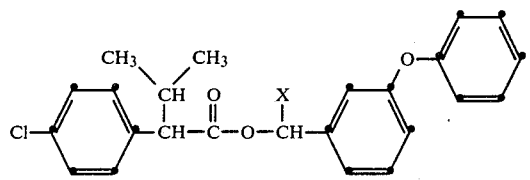

wherein X is chlorine or bromine.

4. A compound according to claim 3 wherein X is bromine.

5. A compound according to claim 3 wherein X is chlorine.

6. A compound of the formula:

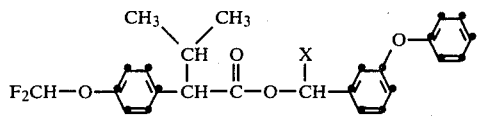

wherein X is chlorine or bromine.

7. A compound according to claim 6 wherein X is bromine.

8. A compound according to claim 6 wherein X is chlorine.

* * * * *